United States Patent [19]

Johansson et al.

[11] Patent Number: 5,656,504
[45] Date of Patent: Aug. 12, 1997

[54] METHOD OF PREVENTING UNDESIRED BINDING IN SOLID PHASE ASSAYS

[75] Inventors: Viveca Johansson, Storvreta; Anita Larsson; Inger Rönnberg, both of Uppsala, all of Sweden

[73] Assignee: Pharmacia Biosensor AB, Uppsala, Sweden

[21] Appl. No.: 424,368

[22] PCT Filed: Oct. 26, 1992

[86] PCT No.: PCT/SE93/00874

§ 371 Date: Apr. 25, 1995

§ 102(e) Date: Apr. 25, 1995

[87] PCT Pub. No.: WO94/10573

PCT Pub. Date: May 11, 1994

[30] Foreign Application Priority Data

Oct. 26, 1992 [SE] Sweden ................................. 9203118

[51] Int. Cl.$^6$ ................................................. G01N 33/543
[52] U.S. Cl. ........................ 436/518; 436/528; 436/529; 436/825; 435/7.92; 435/962; 435/970; 422/82.05; 422/82.06; 422/82.11
[58] Field of Search ........................ 422/82.05, 82.06, 422/82.11; 435/7.92–7.95, 962, 970; 436/518, 548, 528, 529, 531, 825

[56] References Cited

U.S. PATENT DOCUMENTS

| | | | |
|---|---|---|---|
| 4,680,274 | 7/1987 | Sakai et al. | 436/512 |
| 4,829,009 | 5/1989 | Graves | 436/518 |
| 5,147,783 | 9/1992 | Uda et al. | 436/518 X |
| 5,210,020 | 5/1993 | Kondo et al. | 436/518 X |
| 5,242,828 | 9/1993 | Bergström et al. | 435/291 |
| 5,313,264 | 5/1994 | Ivarsson et al. | 356/73 |
| 5,393,659 | 2/1995 | Noah et al. | 436/518 X |
| 5,418,138 | 5/1995 | Miller et al. | 435/963 X |
| 5,441,871 | 8/1995 | Seon | 436/548 X |
| 5,447,837 | 9/1995 | Urnovitz | 436/518 X |

FOREIGN PATENT DOCUMENTS

| | | |
|---|---|---|
| 0372413 | 6/1990 | European Pat. Off. . |
| 0468481 | 1/1992 | European Pat. Off. . |
| 0484765 | 5/1992 | European Pat. Off. . |
| WO90/05305 | 5/1990 | WIPO . |

OTHER PUBLICATIONS

L. Bosato et al., "Incidence and Specificity of Interference in Two–Site Immnoassays," Clinical Chemistry 32(8):1491–1495 (1986).

Merrill et al, Hydrogels in Medicine and Pharmacy, vol. III, Ed. Peppas, N.A., Chapter 1, CRC Press, pp. 1–2 (1986).

Howard C.B. Graves Journal of Immunological Methods, 111 (1988) pp. 157–166.

Victor M. Guzov, Sergey A. Usanov, and Vadim L. Chaschin Journal of Immunological Methods, 145 (1991) pp. 167–174.

Journal of Immunoassay, 11 (2), 139–145 (1990).

Japanese Abstracts vol. 10, No. 250 (P–491) for JP61–79164.

*Primary Examiner*—Carol A. Spiegel
*Attorney, Agent, or Firm*—Birch, Stewart, Kolasch & Birch, LLP

[57] ABSTRACT

In assays of the type which comprise contacting the sample containing the analyte to be detected with a solid phase surface supporting a ligand capable of binding the analyte, undesired binding to the surface is prevented to a substantial degree by adding to the sample one or more components of the material forming the ligand supporting solid phase surface, which components are in at least partially soluble form and capable of interacting with constituents of the sample medium.

25 Claims, 2 Drawing Sheets

METHOD OF PREVENTING UNDESIRED BINDING IN SOLID PHASE ASSAYS

BACKGROUND OF THE INVENTION

1. Field of the Invention

The present invention relates to a novel method of preventing undesired binding to the solid phase in solid phase assays, and especially those based upon mass-measuring techniques such as surface plasmon resonance.

2. Description of Related Art

Undesired non-specific or specific binding from serum or plasma is a common problem in immunological tests and has been described in the literature, especially with regard to label dependent tests, such as RIA, ELISA or FIA. Such undesired binding may cause several problems. For example, in the case of a sandwich type of assay where the labelled antibody binds non-specifically to the solid support, this binding will decrease the signal to noise ratio hampering the performance of the test. Similarly, in assays for detection of specific antibodies corresponding only to a minor fraction of the immunoglobulin contents of the sample, non-specific binding of immunoglobulins contained in the sample to the solid support will negatively affect the performance of the test.

Various means to reduce these types of non-specific binding have been attempted. For instance, treatment of the immobilized capturing antibody surface has been done with serum proteins and non-ionic detergents, as disclosed in e.g. EP-A-0484765 and U.S. Pat. No. 4,829,009, with carboxy containing polymers as disclosed in e.g. EP-A-0372413, as well as with non-ionic block copolymers, as disclosed in e.g. EP-A-0468481. All these examples focus to prevent the non-specific binding of either the immunoreagents used for assaying the analyte or the analyte in the sample.

It is also known to reduce undesired binding by adding an "irrelevant" or non-specific antibody to the sample, i.e. an antibody that is not directed to the immobilized capturing antibody or to the analyte of interest, such irrelevant antibody capturing interfering plasma or serum components thereby at least partially inhibiting undesired binding of such components to the solid phase.

It is readily understood that the problems of undesired binding are especially pronounced in immunoassays based on mass-measuring techniques, i.e. where the mass of adsorbed or bound analyte and/or secondary reagent is measured rather than the intensity of the labels of specifically bound labelled components. One type of such mass-measuring technique is based on evanescent wave sensing, such as methods based on surface plasmon resonance, hereinafter for brevity SPR.

In an SPR based biosensor, changes in the refractive index in a layer close to a thin metal film are detected by the consequential changes of the intensity of a totally reflected light beam, and more particularly by the observed wavelength shifts for the intensity minimum. For a more detailed description of such a biosensor reference can be made to WO 90/05295 relating to an optical biosensor system, and to WO 90/05305 relating to a sensor unit and its use in biosensor systems.

One suitable type of sensing surface for use in SPR biosensors is described in WO 90/05303 and comprises a film of a free electron metal, preferably silver or gold, having one of its faces coated with a densely packed monolayer of specific organic molecules. To this monolayer a biocompatible porous matrix, e.g. a hydrogel, is bound, which matrix is employed for immobilizing a suitable ligand for a target biomolecule to be determined by the particular biosensor. Such a hydrogel may e.g. be based on dextran or a dextran derivative.

In immunoassays of serum or plasma samples with this type of hydrogel-coated sensor having specific antibody ligands immobilized thereto the problem of undesired binding resides in binding of non-analyte components in the sample to the solid phase surface material supporting the ligands. Such undesired binding not only causes a reduced sensitivity of the assay but also causes other problems, which can affect the possibility of regenerating the sensing surface for multiple analysis purposes, i.e. removing bound analyte from antibodies immobilized to the sensing surface to prepare the surface for a new analytical cycle. Further, the background levels will vary with different serum and plasma samples.

The prior art means discussed above for preventing non-specific binding of the analyte or the immunoreagents used for assaying the analyte do not solve these problems. Neither is the addition of irrelevant antibody to the sample as described above sufficient to reduce the problem of undesired binding to the sensing surface to an acceptable level.

SUMMARY OF THE INVENTION

In accordance with the present invention, it has now surprisingly been found that undesired binding to the sensing surface in the above type of immunoassays may be at least substantially reduced by adding directly to the serum or plasma sample a substantially soluble component of the hydrogel, or more generally the solid phase surface material, which component is capable of interacting with constituents of the blood sample medium.

It is believed that the considerable effect obtained by the supplementary addition of the solid phase or carrier surface material component, such as e.g. dextran or a dextran derivative, to the sample may be due to the inhibition of the effects of (i) the possible charges of the solid phase surface material triggering the coagulation system in plasma to clotting, resulting in the precipitation of fibrin on the surface; (ii) ionic interaction between a charged surface material and oppositely charged components, such as proteins, in the blood sample; and/or (iii), depending on the surface material, the possible existence of human low-affinity antibodies or other substances in the sample which could recognize a component of the sensing surface, such as dextran antibodies in the case of a dextran based carrier matrix.

The present invention therefore generally provides a method of preventing undesired (non-specific or specific) binding in assays of the type which comprises contacting the sample containing the analyte to be detected with a solid phase surface supporting a ligand capable of binding the analyte, which method is characterized by adding to the sample one or more components of the material forming the ligand supporting solid phase surface, said components being in at least partially soluble form and capable of interacting with constituents of the sample medium.

The solid phase surface is advantageously of carrier matrix type, the term matrix being to be understood in a broad sense. Such a carrier matrix which, for example, has a thickness from a few angstroms to several thousand angstroms, may be in the form of a hydrogel. For a definition of the term hydrogel it may be referred to Merrill et al. (1986), Hydrogels in Medicine and Pharmacy, Vol. III, Ed. Peppas NA, Chapter 1, CRC Press. The hydrogel may, for example, be a polysaccharide, such as e.g. agarose, dextran, carrageenan, alginic acid, starch, cellulose, or derivatives thereof, such as e.g. carboxymethyl derivatives, or a water-swellable organic polymer, such as e.g. polyvinyl alcohol, polyacrylic acid, polyacrylamide, polyethylene glycol.

As indicated above, polysaccharides of the dextran type, which are non-crystalline in character as in contrast to e.g.

cellulose, have been found to be suitable in biosensor contexts. The term dextran as used herein is to be understood in a broad sense to comprise native as well as depolymerized and synthetic dextrans and modified variants and derivatives thereof. An example of a modified dextran or dextran derivative is carboxymethyl dextran.

The component of the carrier surface material to be added to the sample may be any "building block" thereof that is capable of interacting with the constituents in the sample medium. For a polymeric material, for example, the component may be a polymer or oligomer chain of suitable length to be at least partially, and preferably at least substantially soluble in the sample medium.

In case the surface supports an antibody directed to the analyte to be detected, non-specific antibody is preferably also added to the sample as is per se known in the art. Since such antibody immobilized to the carrier surface is generally of mouse origin, the added irrelevant or non-specific antibody should therefore also preferably be of mouse origin.

In case the sample is a blood sample, whole blood may be used, but it is preferred to use serum or plasma. While serum has been considered to give a lower degree of undesired binding in immunological tests since the coagulation system has been removed, plasma has the advantage of being much more readily prepared, e.g. by anti-coagulation followed by centrifugation, and may therefore be preferred for many applications of the present invention.

The method of the present invention is applicable to immunoassays in general, such as immunoassays, e.g. ELISA and RIA. As indicated above, it is, however, especially useful when a mass-measuring detection technique is used, such as piezoelectric, optical, thermooptical and surface aoustic wave (SAW) methods. Optical methods include reflection optical methods, comprising both internal and external reflection methods, such as ellipsometry, external Brewster angle reflectometry, and evanescent wave reflectometry. The latter includes surface plasmon resonance (SPR) reflectometry, Brewster angle reflectometry, critical angle reflectometry, frustrated total reflection (FTR), evanescent wave ellipsometry, scattered total internal reflection (STIR), optical waveguide sensors, refractometric optical fiber sensors, evanescent wave based imaging, such as critical angle resolved imaging, Brewster angle resolved imaging, SPR angle resolved imaging, etc.

The amounts of carrier surface material component and optionally irrelevant antibody, respectively, to be added to the sample will depend on the particular analytical situation, including the antibodies and carrier surface material components involved, and will readily be determined by the skilled person with guidance of the disclosure herein. For example, in the case of dextran, as a general rule, the concentration of dextran or derivative thereof in the sample should preferably be up to about 2 mg/ml, more preferably in the range from about 0.5 to about 1.5 mg/ml. The concentration of irrelevant antibody should preferably be up to about 200 µg/ml, more preferably in the range from about 5 to about 100 µg/ml. In the particular case of a carboxymethyl dextran surface having mouse monoclonal antibody immobilized thereto and a plasma sample, a suitable addition of irrelevant mouse monoclonal antibody will be to about 100 µg/ml final concentration of the blood sample. A corresponding suitable addition of carboxymethyl dextran will be to about 1 mg/ml final concentration.

In accordance with the present invention, it has moreover been found that undesired binding to the solid phase surface may be further decreased by providing for high ionic strength in the assay without affecting the binding between the immobilized antibody and the analyte of interest in the sample. This is preferably accomplished by the addition of sodium chloride. It is believed that such high ionic strength will inhibit interfering ionic interaction. The ionic strength increasing substance may be added to either the blood sample or, preferably, the drive eluent or buffer in case of flow cell systems, since a salt addition to the blood sample may cause the blood cells to haemolyze due to osmolality change. As an example of a suitable ionic strength increasing substance may be mentioned sodium chloride, and the concentration thereof in the blood sample or drive eluent is preferably in the range from about 0.15 to about 0.7M, e.g. 0.5M. It has also been found that the subclass of the capturing antibody is of importance for the phenomenon of undesired binding. Thus, antibodies of IgG2a and IgG2b type have proved to give a considerably higher degree of undesired binding than antibodies of IgG1 and IgG3 type. It is therefore preferred to use the latter as antibodies, particularly monoclonals, immobilized to the solid phase surface.

BRIEF DESCRIPTION OF THE DRAWING

In the following, the invention is described in more detail, by way of example only, reference being made to the accompanying drawings, wherein.

DESCRIPTION OF THE PREFERRED EMBODIMENTS

EXAMPLE 1

A commercial SPR based biosensor instrument, BIAcore™ (Pharmacia Biosensor AB, Uppsala, Sweden) was used. The sensing surface was Sensor Chip CM5 (Pharmacia Biosensor AB, Uppsala, Sweden), consisting of a glass support with a gold film having a layer of carboxylated dextran covalently bound to the surface of the gold film.

Drive eluent was HBS (10 mM Hepes, 150 mM NaCl, 3.4 mM EDTA, 0.05% Tween®, plus 0.35M sodium chloride, pH 7.4.

Mouse monoclonal IgG1 directed against human luteinizing hormone (LH) (Kabi Pharmacia Diagnostics AB, Uppsala, Sweden), hereinafter referred to as anti-LH, 50 µg/ml in coupling buffer (10 mM Na-acetate, pH 5.0), was imobilized to the dextran layer in accordance with the instrument manufacturer's instructions.

Figure 1:
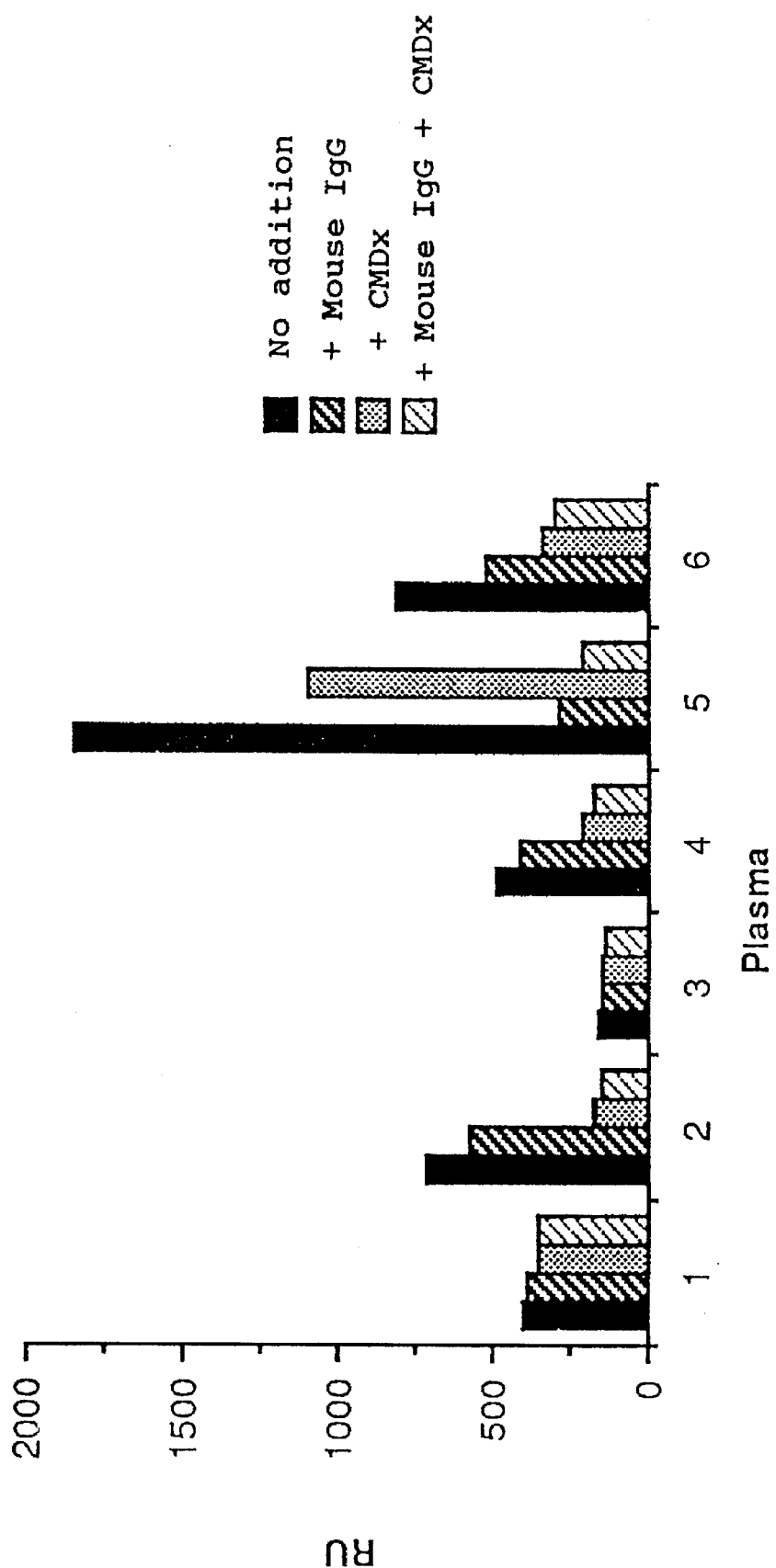
FIG. 1 is a bar chart showing undesired binding as a function of plasma samples from different individuals with and without, respectively, the addition of CM dextran (CMDx) and mouse monoclonal IgG1 (mouse IgG)

To whole blood samples of 2 ml from six different individuals were added either 100 µl of HBS; (ii) 100 µl of HBS containing 200 µg of mouse monoclonal antibody to alfa-feto protein (anti-AFP) (clone 118, Kabi Phamacia Diagnostics AB, Uppsala, Sweden); (iii) 100 µl of HBS containing 2 mg of carboxyethyldextran sodium salt Dx10 (CM dextran) (Fluka, Gemany); or (iv) 100 µl of HBS containing 200 µg of anti-AFP and 2 mg of CM dextran. The final concentrations of anti-AFP and CM dextran in the blood samples were thus 100 µg/ml and 1 mg/ml, respectively. The whole blood samples were centrifugated and the plasma collected. 35 µl of each plasma sample were then injected to the anti-LH coupled surface at a flow rate of 5 µl per minute. The response in resonance units (RU) for each respective plasma sample was read at eight minutes after injection, and the results are presented in FIG. 1. From the figure it is seen that, depending on the sample, the addition of CM dextran alone may reduce the undesired binding by up to 76%. The addition of mouse IgG alone may reduce the undesired binding by up to 85%, and the combined addition of mouse IgG and CM dextran may reduce the undesired binding by up to 88%.

EXAMPLE 2

Figure 2:
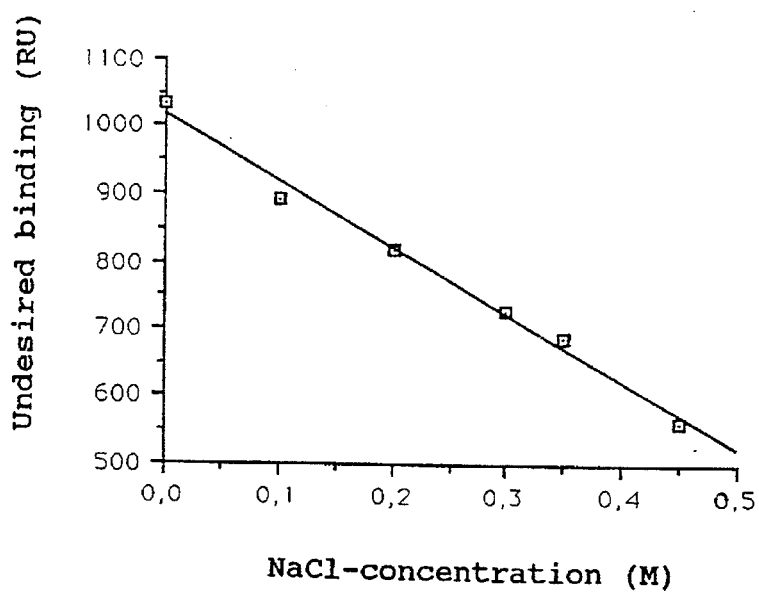
FIG. 2 is a graph showing undesired binding as a function of sodium chloride concentration in a plasma sample.

Using the same biosensor instrument as in Example 1 above, the relation between undesired binding and addition of sodium chloride to the plasma sample was studied. Sodium chloride was added to a plasma sample prepared by centrifugation of human whole blood to the final concentrations of 0.1, 0.2, 0.3, 0.35 and 0.45M, respectively. The dilution was 10% and 10% HBS was therefore added to the zero sample. 35 µl of the plasma were injected into the biosensor instrument for each concentration at a flow rate of 5 µl per minute, and the undesired binding was measured as above. The response for each respective plasma sample was read at eight minutes after injection, and the results are shown in FIG. 2 where the undesired binding (in Resonance Units, RU) is plotted against sodium chloride concentration (M). From the figure it is seen that in the concentration range tested, the undesired binding decreases linearly with the concentration of sodium chloride.

Figure 3:
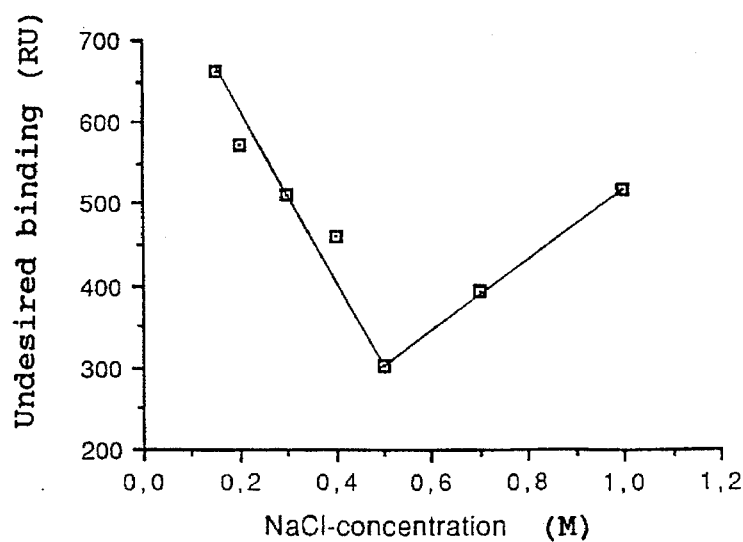
FIG. 3 is a graph showing undesired binding as a function of sodium chloride concentration in the drive eluent.

In the same way as above, the relation between undesired binding and the addition of sodium chloride to the drive eluent was studied, the concentration of sodium chloride in a plasma sample being varied from 0.15M to 1.0M. The results are shown in FIG. 3. As appears therefrom, the undesired binding decreases linearly to 0.5M to then slightly increase.

We claim:

1. A specific binding assay method for determining an analyte in a sample with reduced nonspecific interference from non-analyte constituents in said sample comprising:
   (a) providing a solid phase comprising a polymer surface having immobilized thereto a ligand capable of specifically binding said analyte;
   (b) adding one or more monomeric, oligomeric or polymeric chain fragments of said polymer to said sample wherein said fragments are at least partially soluble in said sample, to form a reaction medium;
   (c) contacting said reaction medium with said solid phase; and
   (d) measuring any binding of said analyte to said contacted solid phase to determine the presence or amount of said analyte in said sample, wherein said nonspecific interference is reduced in that said non-analyte constituents bind to said fragments in said reaction medium rather than to said solid phase.

2. The method according to claim 1, wherein said solid phase surface is provided as a carrier matrix coating said solid phase.

3. The method of claim 2, wherein said carrier matrix is a hydrogel.

4. The method according to claim 3, wherein said hydrogel is dextran or a derivative thereof.

5. The method according to claim 4, wherein said dextran or derivative thereof is present at a final concentration up to about 2 mg/ml in said reaction medium.

6. The method according to claim 4, wherein said dextran or derivative thereof is present at a final concentration of about 0.5 to about 1.5 mg/ml in said reaction medium.

7. The method according to claim 3, wherein said hydrogel is a polysaccharide or a water-swellable organic polymer.

8. The method according to claim 3, wherein said polymer and said fragments are polymeric or oligomeric chains of said hydrogel.

9. The method according to claim 8, wherein said polymeric or oligomeric chain is soluble in said reaction medium.

10. The method according to claim 1, wherein said ligand is an antibody and wherein a nonspecific antibody is further added to said reaction medium.

11. The method according to claim 10, wherein said antibody and said nonspecific antibody are mouse monoclonal antibodies.

12. The method according to claim 10, wherein said nonspecific antibody is present at a final concentration up to about 200 µg/ml in said reaction medium.

13. The method according to claim 12, wherein said nonspecific antibody is present at a final concentration in the range of from about 5 to about 100 µg/ml in said reaction medium.

14. The method according to claim 1, wherein said sample is blood, serum or plasma.

15. The method according to claim 14, wherein said sample is serum or plasma.

16. The method according to claim 1, wherein said measuring step comprises measuring any increase in the mass of said solid phase due to binding thereto of said analyte.

17. The method according to claim 16, wherein said mass measurement is an optical reflection measurement by an evanescent wave sensor.

18. The method according to claim 16, wherein said mass measurement is surface plasmon resonance measurement.

19. The method according to claim 1, further comprising adding an ionic strength increasing agent to said reaction medium in an amount sufficient to inhibit interfering ionic interactions without affecting specific binding between said ligand and said analyte.

20. The method according to claim 19, wherein said ionic strength increasing agent is sodium chloride which is present at a final concentration in the range from about 0.15 to about 0.7M in said reaction mixture.

21. The method according to claim 19, wherein said mass measurement is taken in a flow cell through which a buffer or elution reagent flows and wherein said reaction medium is injected into said flowing buffer or elution agent.

22. The method according to claim 21, wherein said ionic strength agent is provided as part of said flowing buffer or elution reagent.

23. The method according to claim 1, wherein said antibody which is said ligand is an IgG2a or IgG2b antibody.

24. The method according to claim 23, wherein said antibody which is said ligand is a monoclonal antibody.

25. A specific binding assay method for determining an analyte in a sample with reduced nonspecific interference from non-analyte constituents in an aqueous sample containing or suspected of containing the analyte to be detected comprising:
   (a) providing a solid phase surface comprising an organic hydrogel surface having immobilized thereto a ligand capable of specifically binding said analyte;
   (b) adding one or more water soluble monomeric, oligomeric or polymeric fragments of said organic hydrogel to said sample wherein said fragments are at least partially soluble in said sample, to form a reaction medium;
   (c) contacting said reaction medium with said solid phase; and
   (d) measuring any binding of said analyte to said contacted solid phase to determine the presence or amount of said analyte in said sample, wherein said nonspecific interference is reduced in that said non-analyte constituents bind to said fragments in said reaction medium rather than to said solid phase.

* * * * *

UNITED STATES PATENT AND TRADEMARK OFFICE
CERTIFICATE OF CORRECTION

| | |
|---|---|
| PATENT NO. | : 5,656,504 |
| APPLICATION NO. | : 08/424368 |
| DATED | : August 12, 1997 |
| INVENTOR(S) | : Viveca Johansson et al. |

It is certified that error appears in the above-identified patent and that said Letters Patent is hereby corrected as shown below:

Item (30)
Foreign Application Priority Data "Oct. 26, 1992 [SE] Sweden........9203118" should read as --Oct. 26, 1993 [SE]........9203118--

Signed and Sealed this

Seventeenth Day of April, 2007

JON W. DUDAS
*Director of the United States Patent and Trademark Office*